United States Patent
Kim

(10) Patent No.: US 11,766,254 B2
(45) Date of Patent: Sep. 26, 2023

(54) MEDICAL THREE-DIMENSIONAL THREAD MAKING METHOD AND DEVICE USING ULTRASONIC WAVES

(71) Applicant: MEDI FUTURES CO., LTD., Seongnam-si (KR)

(72) Inventor: Ji Hwan Kim, Busan (KR)

(73) Assignee: MEDI FUTURES CO., LTD., Seongnam-si (KR)

( * ) Notice: Subject to any disclaimer, the term of this patent is extended or adjusted under 35 U.S.C. 154(b) by 375 days.

(21) Appl. No.: 16/906,229

(22) Filed: Jun. 19, 2020

(65) Prior Publication Data

US 2020/0315618 A1 Oct. 8, 2020

Related U.S. Application Data

(63) Continuation of application No. PCT/KR2018/010294, filed on Sep. 4, 2018.

(30) Foreign Application Priority Data

Dec. 28, 2017 (KR) ........................ 10-2017-0183107

(51) Int. Cl.
*A61B 17/06* (2006.01)
*A61L 17/10* (2006.01)
(Continued)

(52) U.S. Cl.
CPC ...... *A61B 17/06166* (2013.01); *A61L 17/105* (2013.01); *D02G 3/448* (2013.01);
(Continued)

(58) Field of Classification Search
None
See application file for complete search history.

(56) References Cited

U.S. PATENT DOCUMENTS

2003/0149447 A1* 8/2003 Morency .......... A61B 17/06166
606/228
2009/0076543 A1* 3/2009 Maiorino ................. B26D 3/08
606/228
(Continued)

FOREIGN PATENT DOCUMENTS

EP 3181061 A2 6/2017
JP 2006265796 A 10/2006
(Continued)

OTHER PUBLICATIONS

Machine translation of JP2012232120 (Year: 2012).*
(Continued)

*Primary Examiner* — Shawn Mckinnon
(74) *Attorney, Agent, or Firm* — Dinsmore & Shohl LLP; Yongsok Choi, Esq.

(57) ABSTRACT

A three-dimensional thread making method using ultrasonic waves is provided. The method includes inserting a yarn into a position corresponding to an engraved pattern of a mold base between an ultrasonic wave generator and the mold base at positions adjacent to each other, applying ultrasonic waves to the yarn while the ultrasonic wave generator pressurizes the yarn, and injecting a medical anti-loosening member made in a form of the engraved pattern due to the ultrasonic waves. The medical anti-loosening member includes a medical three-dimensional thread formed to have a plurality of protrusions facing each other on both sides and a medical anti-loosening screw.

6 Claims, 4 Drawing Sheets

(51) Int. Cl.
    *D02G 3/44*     (2006.01)
    *D02J 3/02*     (2006.01)
    *A61B 17/00*     (2006.01)
    *D02J 3/00*     (2006.01)

(52) U.S. Cl.
    CPC ....... *D02J 3/02* (2013.01); *A61B 2017/00526* (2013.01); *A61B 2017/0619* (2013.01); *A61B 2017/06176* (2013.01); *D02J 3/00* (2013.01); *D10B 2401/041* (2013.01)

(56) References Cited

U.S. PATENT DOCUMENTS

| | | | |
|---|---|---|---|
| 2016/0106411 A1 | | 4/2016 | Rousseau |
| 2016/0106422 A1* | | 4/2016 | Lindh, Sr. .......... A61B 17/0401 606/228 |

FOREIGN PATENT DOCUMENTS

| | | | |
|---|---|---|---|
| JP | 2012130669 A | | 7/2012 |
| JP | 2012232120 | * | 11/2012 |
| KR | 101057377 B1 | | 8/2011 |
| KR | 101352649 B1 | | 1/2014 |
| KR | 101581865 B1 | | 12/2015 |
| KR | 101642962 B1 | | 7/2016 |
| KR | 1020170084097 A | | 7/2017 |
| KR | 101806150 B1 | | 12/2017 |

OTHER PUBLICATIONS

European Search Report of EP Application No. 18894702.2 dated Aug. 30, 2021.
International Search Report of PCT/KR2018/010294 dated Dec. 10, 2018.
Examination Report of EP Application No. 18 894 702.2 dated Feb. 23, 2023.

\* cited by examiner

200

MEDICAL THREE-DIMENSIONAL THREAD MAKING METHOD AND DEVICE USING ULTRASONIC WAVES

CROSS-REFERENCE TO RELATED APPLICATION

This application is a continuation of International Patent Application No. PCT/KR2018/010294 filed on Sep. 4, 2018, which claims priority to Korean Patent Application No. 10-2017-0183107 filed in the Korean Intellectual Property Office on Dec. 28, 2017, the entire contents of which are incorporated herein by reference.

BACKGROUND OF THE INVENTION

1. Field of the Invention

The present invention relates to medical three-dimensional thread making method and device using ultrasonic waves, and more particularly, to method and device for molding a suture thread used for cosmetic and medical purposes by using ultrasonic waves.

2. Description of the Related Art

In the related art, medical threads were mainly used for the purpose of suturing in surgery, and a technology for lifting loose skin and tissues of the face, chin, neck, abdomen, vagina, chest, hips, and so on and for pulling and straightening wrinkles with a needle and a thread without using a knife is in the spotlight because there is no need to cut the skin excessively, scarring may be minimized, and there is less bleeding or swelling from surgery.

Natural and synthetic materials may be used as the material, and materials of a natural material absorbent medical thread include catgut, chromic, gut, and so on, and materials of a synthetic material absorbent medical thread include polyglycolic acid (dexone, mexone), polyglactin (biacryl), and polydioxanone (PDS), and so on. A material of a natural material non-absorbent medical thread includes silk, and materials of a synthetic material non-absorbent medical thread include polyester (Dacron), polypropylene (proline), polyamide (nylon), and e-PTFE (Gore-Tex).

In the related art, protrusions are formed on a surface of a medical thread to be used, and the making method of the related art includes thermal molding or molding through compression, and thereby, there are problem that a surface of a thread is uneven, molding of a fine shape is restrictive, and lint is formed around the protrusion, and also, there are problems that deformation occurs during thermal molding due to the nature of a polydioxane (PDO) material and strength is weakened.

In addition, the method of the related art using ultrasonic waves includes attaching plastic materials through vibration of ultrasonic waves as an ultrasonic welding method. That is, the ultrasonic welding technology is a method of converting electrical energy into mechanical vibrational energy to generate instantaneous strong frictional force on a fusion bonding surface, and due to this, a bonding surface of a workpiece is melt-bonded and a strong molecular bonding is made.

A method of using ultrasonic waves used for industrial purposes is the ultrasonic welding method described above and is not used to change a form into a desired form of a specific workpiece.

SUMMARY OF THE INVENTION

The present invention is to solve the problems of the related art described above and relates to a method and a making device for transforming a yarn by using ultrasonic vibration.

The present invention provides a method of injecting a thread by using an ultrasonic wave generator, and is aimed to provide method and device of making medical thread (suture thread) which may be transformed into a more sophisticated form than the medical thread (suture thread) of the related art and resolve factors of deterioration in physical strength, and a thickness or a length of a protrusion (scale) of which is precisely adjusted down to two decimal places.

A method of making a medical anti-loosening member using ultrasonic waves according to the present invention includes (a) a step of inserting a yarn into a position corresponding to an engraved pattern of a mold base between an ultrasonic wave generator and the mold base adjacent to each other; (b) a step of applying ultrasonic waves to the yarn while the ultrasonic wave generator pressurizes the yarn; and (c) a step of injecting a medical anti-loosening member made in a form of the engraved pattern due to the ultrasonic waves, wherein the medical anti-loosening member includes a medical three-dimensional thread formed to have a plurality of protrusions facing each other on both sides and a medical anti-loosening screw.

According to an embodiment of the present invention, in making a medical three-dimensional thread used for medical or cosmetic purposes, a satisfactory error rate of 3% to 5% may be achieved by using a method and device for making a medical three-dimensional thread with high tensile force and holding force.

It is possible to form approximately twice as many protrusions as a medical thread of the related art and to remove a factor that reduces a physical strength by not scratching or applying a knot to a yarn by using ultrasonic waves.

Due to this, it is possible to obtain more effective efficacy in performing a lifting procedure, and rigid fixing and maintenance may be possible compared with a device of the related art.

Compared to the cutting method of the related art using heat and pressure of a mold, a cog form and various three-dimensional forms may be made by applying an ultrasonic vibration to a material and putting the particles in a mold of an ultrasonic die.

A method in which a yarn is heated to be flattened by a roller and the flattened yarn is pressurized into a mold to be cut into a mold form is used in the related art, while the yarn is heated, a material expands in volume and density resulting in weakness of physical properties of a raw material by approximately 30%, and if the flattened yarn that is expanded by applying heat is pressurized into a cog-shaped mold to be cut, fluffs are formed at the end of the cog which causes difficulty in forming a sharp point at the end of the cog, but in a processing method using an ultrasonic vibration, the yarn is put into a cog-shaped mold and an ultrasonic vibration is applied thereto in a short time, thereby, minimizing heat or artificial stimulation, and thus, there is little deformation of the raw material of the yarn, and the existing ability of strength and physical properties may be maintained.

DETAILED DESCRIPTION OF THE EMBODIMENT

Figure 1:
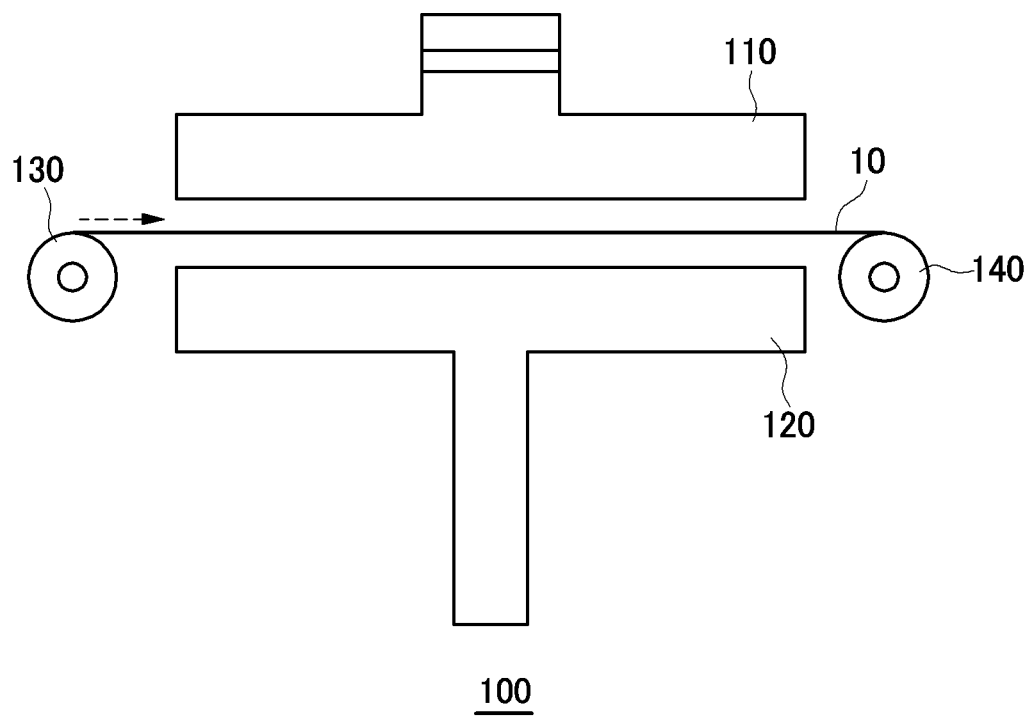
FIG. 1 is a side view of a making device for explaining a medical three-dimensional thread making method and device according to a first embodiment of the present invention.

The present invention may be variously transformed and have various forms, and implementation examples (or embodiments) will be described in detail in the specification. However, this is not intended to limit the present invention to specific disclosing mode, and should be understood to include all changes, equivalents, and substitutes included in the idea and scope of the present invention.

Throughout the specification, when it is described that a portion is "connected" to another portion, this includes not only a case of being "directly connected" but also a case of being "electrically connected" with another element therebetween. In addition, when it is described that a portion "includes" a certain configuration element, this means that the portion may further include another configuration element, not exclude another configuration element, unless specifically stated otherwise.

In addition, each drawing illustrates that configuration elements are exaggeratedly large (or thick) or small (or thin), or are simply expressed in size or thickness in consideration of convenience of understanding, and the protection scope of the present invention should not be construed as being limited thereby.

The terms used in the present specification are only used to describe specific implementation examples (aspects) (or embodiments) and are not intended to limit the present invention. Singular expressions include plural expressions unless the context clearly indicates otherwise. In the present application, terms such as ~include~ or ~configured~ are intended to designate the existence of features, numbers, steps, operations, configuration elements, components, or combinations thereof described in the specification, and it should be understood that one or more other features or the existence or addition possibilities of numbers, steps, operations, configuration elements, components, or combinations thereof are not excluded in advance.

Unless otherwise defined, all terms, which are used herein and include technical or scientific terms, have the same meaning as commonly understood by those skilled in the art to which the present invention belongs. Terms, such as those defined in a commonly used dictionary, should be construed as having meanings consistent with meanings in the context of related technologies, and should not be construed as ideal or excessively formal meanings unless explicitly defined in the present application.

In the present specification, reference numerals are separately referred to for the description of the first to fourth embodiments and are not limited to the making order, and names thereof may not match in the detailed description and claims of the specification.

In addition, since devices having the same function are differently referred to in order to describe the second and third embodiments, in other parts except for the paragraphs describing the second or third embodiments, description will be made with reference to the reference numerals in FIG. 1 illustrating the first embodiment.

The present invention relates to a method and device for molding a thread (suture thread) used for medical purposes according to the application by using ultrasonic waves.

In the present specification, the thread used for medical purposes is represented as a three-dimensional thread. However, the three-dimensional thread means the same object as being represented by a cog (COG) thread, a surgical thread, a medical thread, and a suture thread in the related art.

The engraved pattern referred to below means a shape of the pattern illustrated in FIG. 2.

Figure 2:
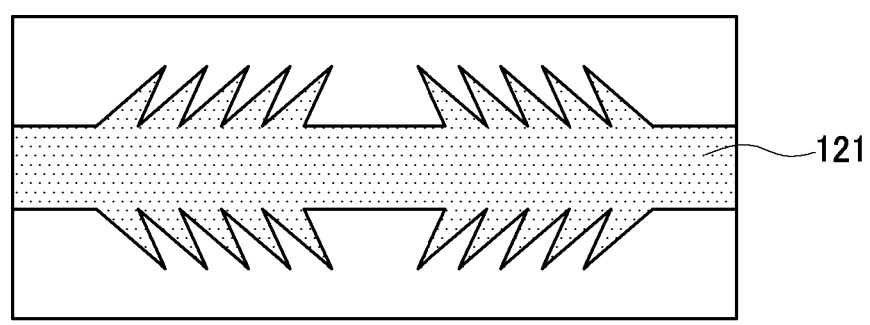
FIG. 2 is an upper side view of a mold base of a making device for explaining medical three-dimensional yarn making method and device according to the first embodiment of the present invention.

Additionally, although only the engraved pattern is formed in FIG. 2, one or more engraved patterns and one or more embossed patterns may be additionally provided. That is, when it is described that a three-dimensional thread is made through the central engraved pattern, one or more embossed patterns and engraved patterns are additionally provided on both sides of the central engraved pattern, and thus, a main body section of a structure of a device and the central engraved pattern may be configured to be slightly spaced apart.

Hereinafter, three-dimensional thread making method and device according to the present invention will be described in detail with reference to the accompanying drawings.

Three-dimensional thread making method and device according to a first embodiment of the present invention will be described in detail with reference to FIGS. 1 and 2.

Bio-absorbable and non-absorbable medical polymers may be used as a raw material of a medical suture thread, and more specifically, a bio-absorbable medical polymer made of any one selected from a group composed of polydioxanone (PDO), poly-(1-lactic)acid, poly-glycolic acid, polycaprolactone, and copolymers thereof, and a bio-absorbable medical polymer made of any one selected from a group composed of polypropylene, nylon, and a mixture thereof.

In the embodiment of the present invention, a yarn 10 is a thermoplastic resin or an ultrasonic plastic resin, and polydioxanone (PDO) may also be utilized as the yarn, and a making method thereof will be described. However, the method is only an embodiment of the present invention, a raw material is not limited thereto, and any one of the above-described raw materials may be utilized.

A first yarn making device 100 according to a first embodiment of the present invention may include an ultrasonic wave generator 110 that generates ultrasonic waves and pressurizes the yarn, and a mold base 120 in which a three-dimensional thread shape is engraved with an engraved pattern 121.

In addition, a yarn insertion section 130 that inserts a yarn, and a yarn injection section 140 that discharges a three-dimensional yarn may be provided in the form of a roller to be rotatable.

At this time, the yarn 10 is fixed through the yarn insertion section 130 and the yarn injection section 140 and may be rotated in one direction to move the yarn 10.

A three-dimensional yarn making method using ultrasonic waves according to the first embodiment of the present invention includes inserting the yarn 10 at a position corresponding to the engraved pattern 121 of the mold base 120 between the ultrasonic wave generator 110 and the mold base 120 disposed at positions adjacent to each other, applying ultrasonic waves to the yarn 10 while the ultrasonic wave generator 110 pressurizes the yarn 10, and injecting the three-dimensional thread made in a shape of the engraved pattern 121 through ultrasonic waves, and the three-dimensional thread may be made to have a plurality of protrusions (scales) facing each other at both sides.

That is, a medical anti-loosening member including the medical three-dimensional thread made as described above and a medical anti-loosening screw may be made. At this time, the medical anti-loosening screw may be made in a form in which screw threads are formed instead of the protrusions on the medical three-dimensional thread.

The ultrasonic wave generator 110 is formed at an upper portion in the first yarn making device 100 and may be spaced apart from the mold base 120 fixed to the ground.

At this time, the ultrasonic wave generator and the mold base are formed in a plate shape and may be disposed to share a central axis. That is, the ultrasonic wave generator and the mold base have the same central axis and may be disposed side by side in one direction.

When the yarn 10 is inserted, the ultrasonic wave generator 110 may descend by a distance that may be in contact with the mold base 120 to pressurize the inserted yarn 10 and generates ultrasonic waves to be applied to the yarn.

The yarn 10 is inserted through the yarn insertion section 130 to be fixed to correspond to a region where the engraved pattern 121 of the mold base 120 is located, and a width of the yarn 10 may be greater than a width of the engraved pattern 121.

When the yarn 10 is located on the engraved pattern 121 of the fixed mold base 120, the above-described ultrasonic wave generator 110 operates, and a three-dimensional yarn may be made.

At this time, the ultrasonic wave emitted by the ultrasonic wave generator 110 is 2 to 4 kHz, and preferably may be 2.5 to 3 kHz. The yarn may be made of a polydioxane (PDO) material and may be made of an ultrasonic plastic resin or a thermoplastic resin, and when heat of 106° C. or higher is applied due to characteristics of PDO, durability (strength) of the yarn 10 may be reduced, but vibration due to ultrasonic waves of 2.5 to 3 kHz according to the first embodiment of the invention does not generate heat to a melting point of the PDO, and thus, a shape may be changed within a range that does not impair durability.

That is, a shape change of the yarn 10 is made by melting a solid yarn by vibrating molecules composing the yarn through ultrasonic waves, and through this process, a three-dimensional yarn that fits the engraved pattern 121 may be made.

Figure 3:
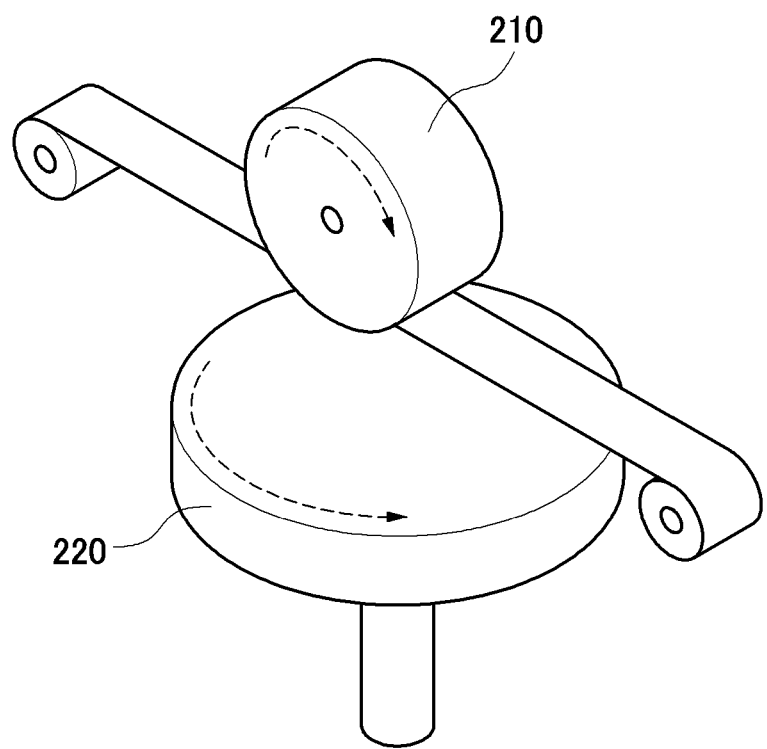
FIG. 3 is a side view of a making device for explaining medical three-dimensional yarn making method and device according to a second embodiment of the present invention.

Hereinafter, a second embodiment of the present invention will be described in detail with reference to FIG. 3.

A second thread making device 200 according to the second embodiment of the present invention includes the same configuration as the first thread making device 100 but may have differences in position and operation method.

The mold base 210 may have the form of a roller that rotates in place in a clockwise or counterclockwise direction, a curved surface of the mold base 210 is configured to be in contact with the ultrasonic wave generator 220, and an engraved pattern may be formed on the curved surface.

At this time, unlike the first yarn making device 100, the mold base 210 is located at an upper portion and the ultrasonic wave generator 220 is located at a lower portion, but the ultrasonic wave generator 220 is configured to rotate in place in a direction opposite to the mold base 210, a plane of the ultrasonic wave generator 220 is configured to be in contact with the curved surface of the mold base 210, and the yarn 10 may be inserted into a region where the mold base 210 and the ultrasonic wave generator 220 are in contact with each other.

In addition, the mold base 210 is in contact with a position spaced apart from a central point of the plane of the ultrasonic wave generator 220, and the ultrasonic wave generator 220 may generate ultrasonic waves such that the ultrasonic waves are applied to the position of the inserted yarn 10.

For example, the mold base 210 may be located at an upper portion of the second thread making device 200, may have a shape of a roller in which a shape of the three-dimensional thread is engraved with the engraved pattern on the curved surface, and be formed in a structure that may pressurize the yarn 10 while rotating in a clockwise direction. In addition, in FIG. 3, a configuration element corresponding to the reference numeral 210 may be an ultrasonic wave generator, and a configuration element corresponding to the reference numeral 220 may also correspond to a mold base.

In addition, the ultrasonic wave generator 220 may be located at a lower portion of the second thread making device 200, may be configured to have a plate shape in which the ultrasonic wave generator is in contact with one region of the mold base 210, and may be formed in a shape in which, while the ultrasonic wave generator rotates counterclockwise, a plane portion thereof is in contact with the mold base 210 to pressurize the yarn, the ultrasonic wave generator generates ultrasonic waves in a region where the yarn 10 is pressurized and applies the ultrasonic waves to the yarn 10.

Figure 4:
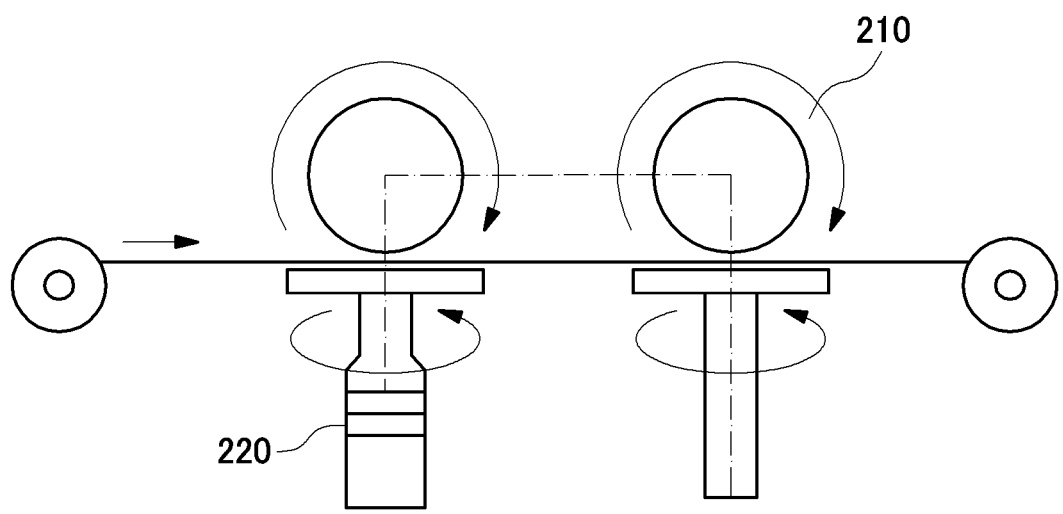
FIG. 4 is a side view illustrating medical three-dimensional yarn making method and device according to according to the second embodiment of the present invention.

On the other hand, as a further embodiment of the present invention, as illustrated in FIG. 4, a thread making device having a structure including a roller, the ultrasonic wave generator 220, and the mold base 210 may be configured as illustrated in FIG. 4. For example, after the process of pressurizing the yarn through the roller is performed at a front stage, a three-dimensional thread may be made according to the engraved pattern through the mold base 210 at a rear stage. At this time, structures of the front stage and the rear stage may be configured to be rolled at an upper portion and a lower portion in the same way.

Figure 5:
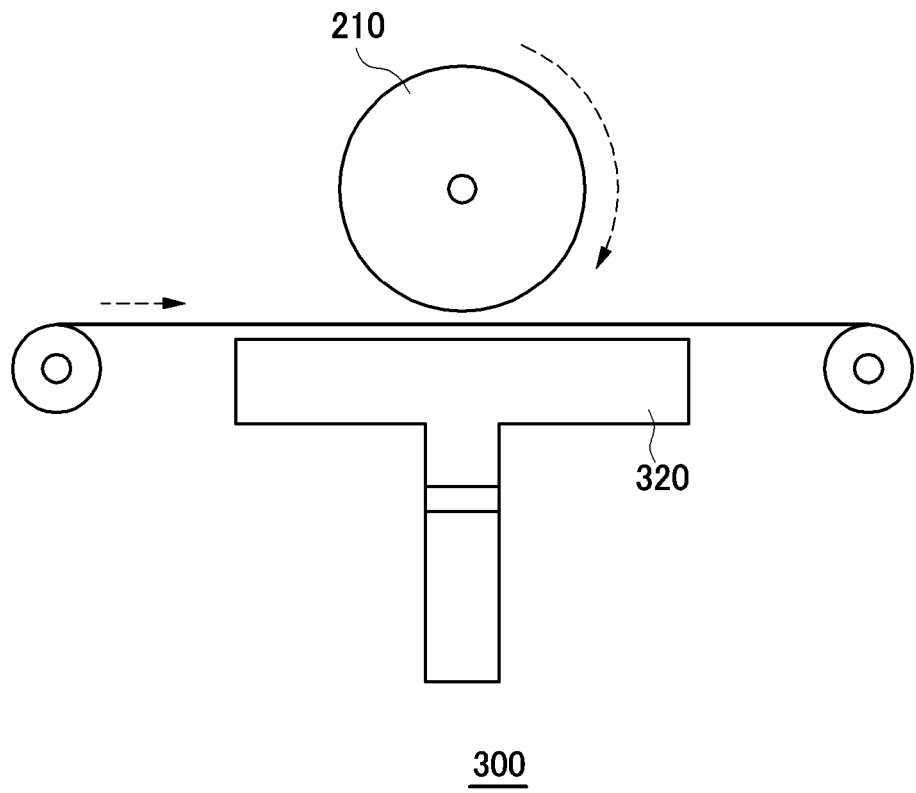
FIG. 5 is a side view of a making device for explaining medical three-dimensional yarn making method and device according to a third embodiment of the present invention.

A third embodiment of the present invention will be described with reference to FIG. 5.

A third yarn making device 300 according to the third embodiment of the present invention has the same configuration and position as the second yarn making device 200 and may differ in an operation method.

The mold base 210 may be formed to be in contact with an ultrasonic wave generator 320 at a position adjacent to a central point of a plane of the ultrasonic wave generator 320 and may be configured to rotate in place.

At this time, the ultrasonic wave generator 320 may be configured in a fixed form without rotation.

That is, the mold base 210 having the form of a roller and having the engraved pattern formed in a curved surface is configured in the form capable of rotating in place so as to be in contact with a region of the plane of the fixed ultrasonic wave generator 320, and may be configured in the form in which the yarn 10 is inserted into a region where the ultrasonic wave generator 320 and the mold base 210 in contact with each other. In addition, the mold base 210 may be configured to reciprocate in one direction on the ultrasonic wave generator 320.

Hereinafter, a fourth thread making device according to a fourth embodiment of the present invention will be described with reference to FIG. 6.

Figure 6:
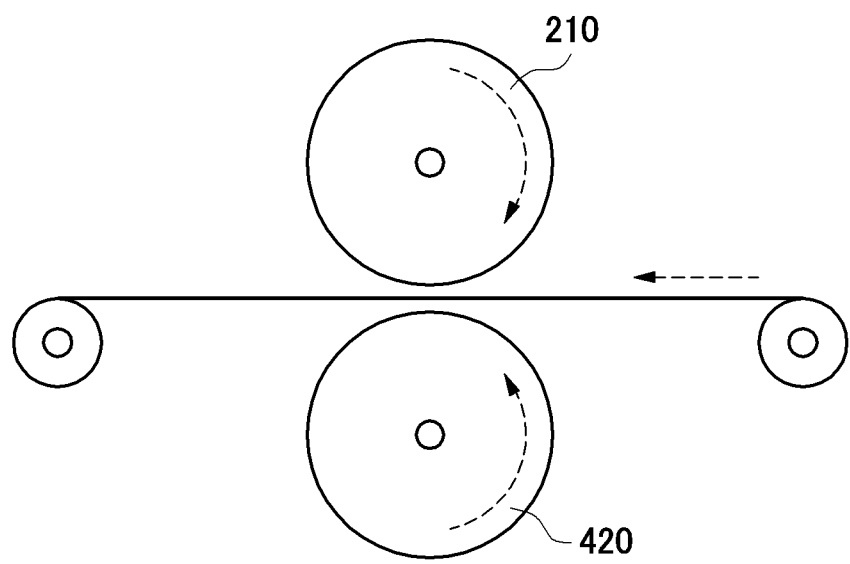
FIG. 6 is a side view of a making device for explaining medical three-dimensional yarn making method and device according to according to a fourth embodiment of the present invention.

As illustrated in FIG. 6, the fourth thread making device may be configured with two rollers, the roller located at an upper portion may include a mold base 210, and the roller located at a lower portion may be configured by an ultrasonic wave roller 420 including an ultrasonic wave generator.

The roller located at the upper portion and the roller located at the lower portion rotate in directions opposite to each other and may make the medical three-dimensional yarn in the same manner as in the embodiments described above.

Figure 7:
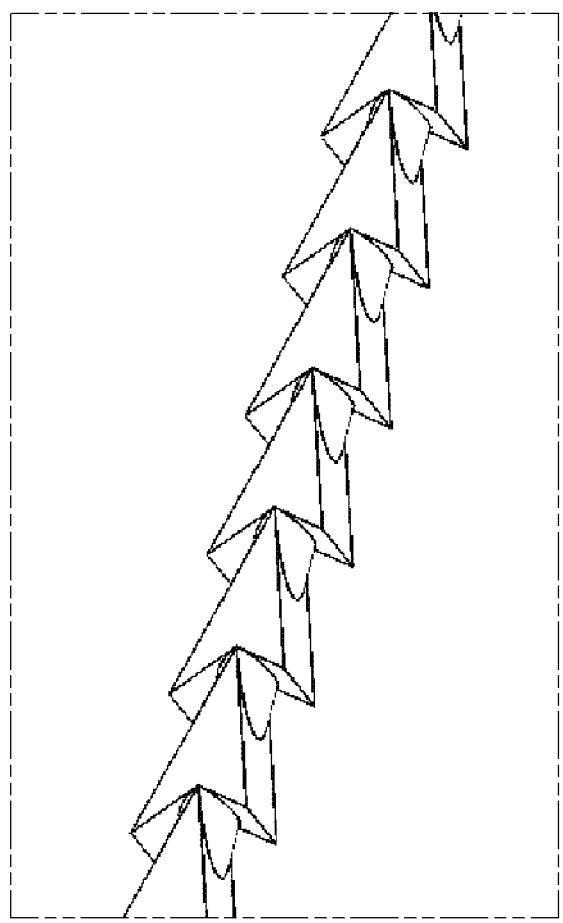
FIG. 7 is a perspective view of a medical three-dimensional thread made by medical three-dimensional yarn making method and device according to the first to fourth embodiments of the present invention.

FIG. 7 is a perspective view of the medical three-dimensional yarn made according to the embodiments described above, the medical three-dimensional yarn may be molded in an elaborate form unlike a yarn of the related art, and protrusions of the yarn may be formed to have a predetermined thickness. In addition, the mold base may be formed such that a transverse cross-section or a longitudinal cross-section of the protrusion has a rectangular shape.

When viewed from a side, one side of the protrusion has a rectangular shape and may be symmetrical left and right.

The protrusion is formed to extend from a body section, formed in a triangular shape as illustrated in the figure, an internal angle formed by the longest side of the protrusion and the body section is formed as an acute angle, an internal angel formed by the shortest side of the protrusion and the body section is formed as an obtuse angle, and thus, the projections face the center.

Specifically, the three-dimensional yarn made by the making method of the present invention and the three-dimensional yarn of the related art are compared with each other as follows. Since the three-dimensional yarn of the present invention may be made very precisely by using ultrasonic waves, the three-dimensional yarn may be made in a smaller and more precise pattern than the three-dimensional yarn of the related art.

The above description of the present invention is for illustration only, and those skilled in the art to which the present invention belongs may understand that the present invention is easily modified to other specific forms without changing the technical idea or essential features of the present invention. Therefore, it should be understood that the embodiments described above are illustrative in all respects and not restrictive. For example, each configuration element described as a single type may be configured in a distributed manner, and similarly, each configuration element described in a distributed manner may be configured in a combined form.

The scope of the present invention is indicated by the following claims rather than the above detailed description, and all the changed or modified forms derived from the meaning and scope of the claims and their equivalent concepts should be interpreted as being included in the scope of the present invention.

DESCRIPTION OF SYMBOLS

100: first yarn making device 10: yarn
110: ultrasonic wave generator (1) 120: mold base (1)
121: engraved pattern
130: yarn insertion section 140: yarn injection section
200: Second yarn making device
210: mold base (2) 220: ultrasonic wave generator (2)
300: third yarn making device
320: ultrasonic wave generator (3)
420: ultrasonic roller

What is claimed is:

1. A thread making method using ultrasonic waves, the method comprising:
   (a) inserting a yarn into a position corresponding to a pattern of a mold base between an ultrasonic wave generator and the mold base adjacent to each other;
   (b) applying ultrasonic waves to an entire portion of the yarn disposed between the mold base and the ultrasonic wave generator while the ultrasonic wave generator contacts and pressurizes the entire portion of the yarn disposed between the mold base and the ultrasonic wave generator; and
   (c) forming a medical anti-loosening member with a plurality of protrusions around a body made in a form of the pattern due to the ultrasonic waves,
   wherein the pattern of the mold base is a thread having a plurality of protrusions facing each other on both sides,
   wherein the pattern of the mold base is composed of a combination of one or more engraved patterns and one or more embossed patterns,
   wherein the step (c) further comprises making the medical anti-loosening member corresponding to the pattern by vibrating molecules configuring the yarn by using the ultrasonic waves to melt a solid yarn, and
   wherein the ultrasonic wave generator and the mold base are formed in a plate shape and are disposed to share a central axis.

2. The thread making method of claim 1, wherein the yarn is formed of an ultrasonic plastic resin or a thermoplastic resin.

3. The thread making method of claim 2, wherein the yarn is formed of a polydioxane (PDO) material.

4. The thread making method of claim 1, wherein a frequency of the ultrasonic wave generated by the ultrasonic wave generator is 2 to 4 kHz.

5. The thread making method of claim 1, wherein the mold base is formed such that each of the plurality of protrusions has a rectangular cross-section.

6. The thread making method of claim 1, wherein the plurality of protrusions symmetrically formed with respect to a longitudinal axis of the yarn.

* * * * *